United States Patent
Krämer et al.

(10) Patent No.: US 10,813,602 B2
(45) Date of Patent: Oct. 27, 2020

(54) PATIENT SUPPORT APPARATUS WITH SIX DEGREES OF FREEDOM

(71) Applicants: Alexander Krämer, Irchenrieth (DE); Wolfgang Neuber, Pressath (DE)

(72) Inventors: Alexander Krämer, Irchenrieth (DE); Wolfgang Neuber, Pressath (DE)

(73) Assignee: Siemens Healthcare GmbH, Erlangen (DE)

( * ) Notice: Subject to any disclaimer, the term of this patent is extended or adjusted under 35 U.S.C. 154(b) by 529 days.

(21) Appl. No.: 15/719,939

(22) Filed: Sep. 29, 2017

(65) Prior Publication Data

US 2018/0092611 A1   Apr. 5, 2018

(30) Foreign Application Priority Data

Oct. 4, 2016   (DE) .................... 10 2016 219 162

(51) Int. Cl.
*A61B 6/04*   (2006.01)
*A61G 7/015*  (2006.01)
(Continued)

(52) U.S. Cl.
CPC .......... *A61B 6/0407* (2013.01); *A61B 6/0478* (2013.01); *A61G 7/015* (2013.01);
(Continued)

(58) Field of Classification Search
CPC .... A61B 6/0407; A61B 6/0478; A61G 7/008; A61G 7/012; A61G 7/018; A61G 7/015;
(Continued)

(56) References Cited

U.S. PATENT DOCUMENTS 6,015,130 A * 1/2000 Kigel ...................... A47C 1/06
                                                        248/404
6,038,718 A * 3/2000 Pennington .............. A61B 6/04
                                                          5/608

(Continued)

FOREIGN PATENT DOCUMENTS

CN         1874727 A      12/2006
CN       102947061 A       2/2013
(Continued)

OTHER PUBLICATIONS

Chinese Office Action for Chinese Application No. 201710897593.X dated Aug. 26, 2019.

(Continued)

*Primary Examiner* — Robert G Santos
*Assistant Examiner* — Rahib T Zaman
(74) *Attorney, Agent, or Firm* — Lempia Summerfield Katz LLC

(57) ABSTRACT

A patient support apparatus including a patient couch and a single supporting pillar on which the patient couch is arranged in an adjustable and cantilevered manner, is provided. The apparatus includes a first rotary frame and a second rotary frame. The first rotary frame rotates about a first axis and encloses the supporting pillar. The second rotary frame rotates about a second axis, rotatably encloses the first rotary frame, and is fixed to the patient couch. The first rotary frame and the second rotary frame form a gimbal mount for the patient couch.

18 Claims, 2 Drawing Sheets

(51) Int. Cl.
*A61N 5/10* (2006.01)
*A61G 7/05* (2006.01)
*A61G 7/005* (2006.01)

(52) U.S. Cl.
CPC ............ *A61N 5/1049* (2013.01); *A61G 7/005* (2013.01); *A61G 7/0513* (2016.11); *A61N 5/107* (2013.01)

(58) Field of Classification Search
CPC ...... A61G 7/0513; A61G 7/005; A61G 13/02; A61G 13/04; A61G 13/06; A61G 13/08; A61N 5/1049; A61N 5/107
See application file for complete search history.

(56) References Cited

U.S. PATENT DOCUMENTS

| | | | |
|---|---|---|---|
| 7,305,727 B2 | 12/2007 | Horlin | |
| 8,424,133 B1* | 4/2013 | Rossi | A61B 6/0442 5/601 |
| 9,301,897 B2* | 4/2016 | Jackson | A61G 13/08 |
| 9,549,863 B2* | 1/2017 | Jackson | A61G 13/08 |
| 2003/0061662 A1* | 4/2003 | Strobel | A61G 13/02 5/618 |
| 2005/0015878 A1* | 1/2005 | Bannister | A61G 13/02 5/618 |
| 2005/0262635 A1 | 12/2005 | Wing | |
| 2007/0094796 A1 | 5/2007 | Bartels | |
| 2012/0144589 A1* | 6/2012 | Skripps | A61G 13/04 5/624 |
| 2013/0087004 A1 | 4/2013 | Neumann | |
| 2013/0111666 A1* | 5/2013 | Jackson | A61G 13/0036 5/601 |
| 2013/0269710 A1* | 10/2013 | Hight | A61G 13/04 128/845 |
| 2015/0113733 A1* | 4/2015 | Diel | A61G 13/04 5/610 |
| 2016/0193099 A1* | 7/2016 | Drake | A61G 13/125 5/624 |

FOREIGN PATENT DOCUMENTS

| | | | |
|---|---|---|---|
| CN | 105664363 A | 6/2016 | |
| EP | 1297812 A1 | 4/2003 | |

OTHER PUBLICATIONS

German Office Action for related German Application No. 10 2016 219 162.4 dated Jul. 12, 2017, with English translation.

* cited by examiner

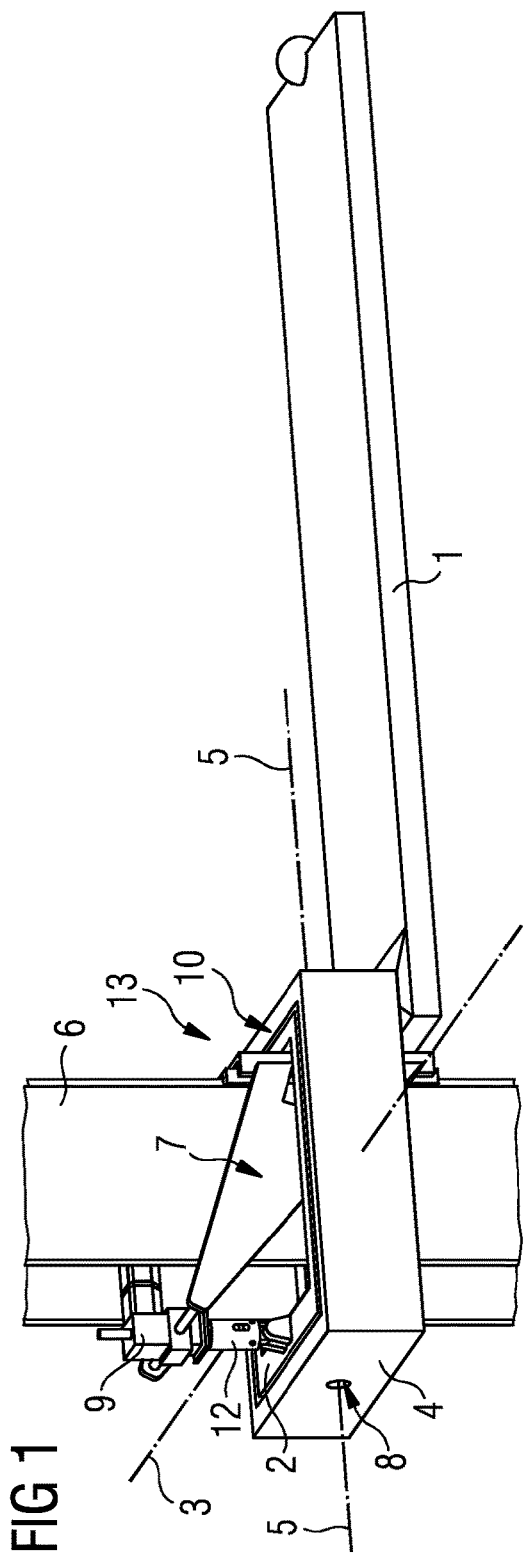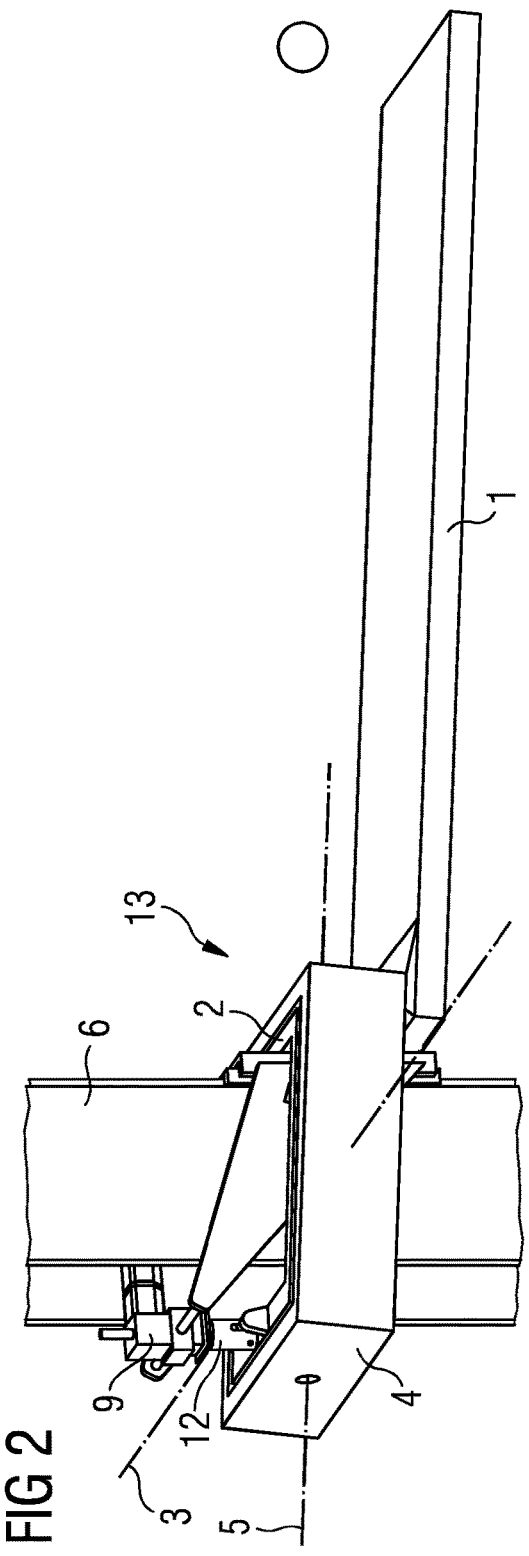

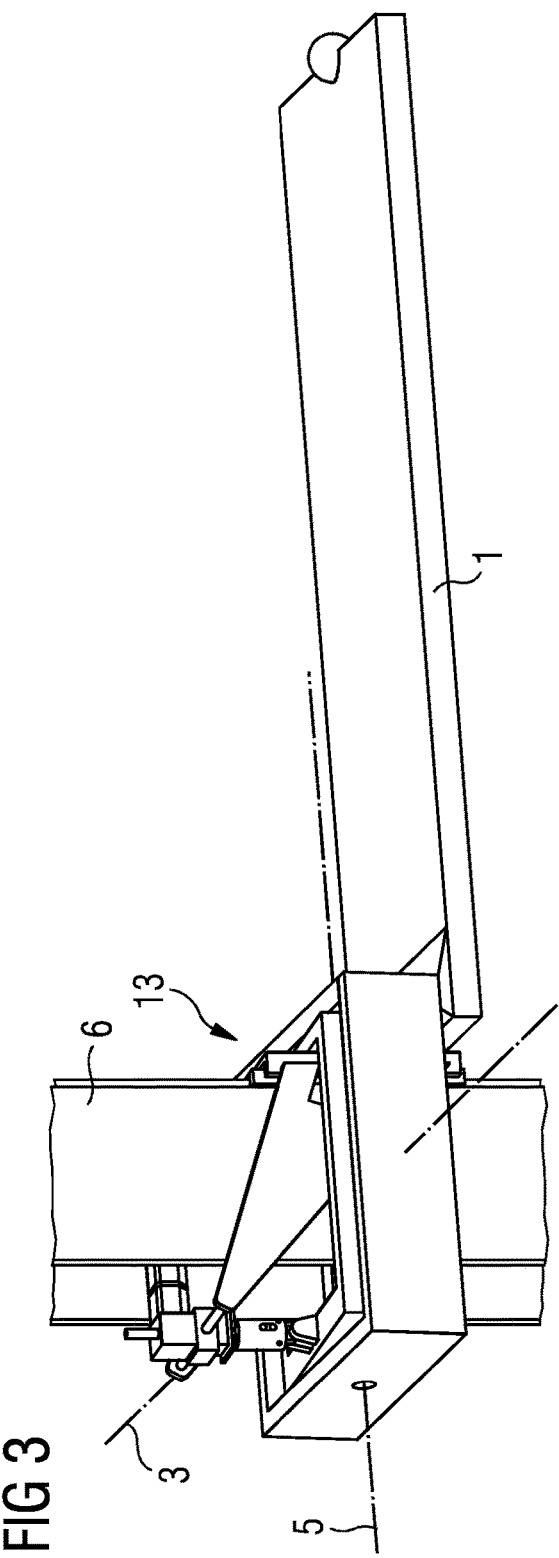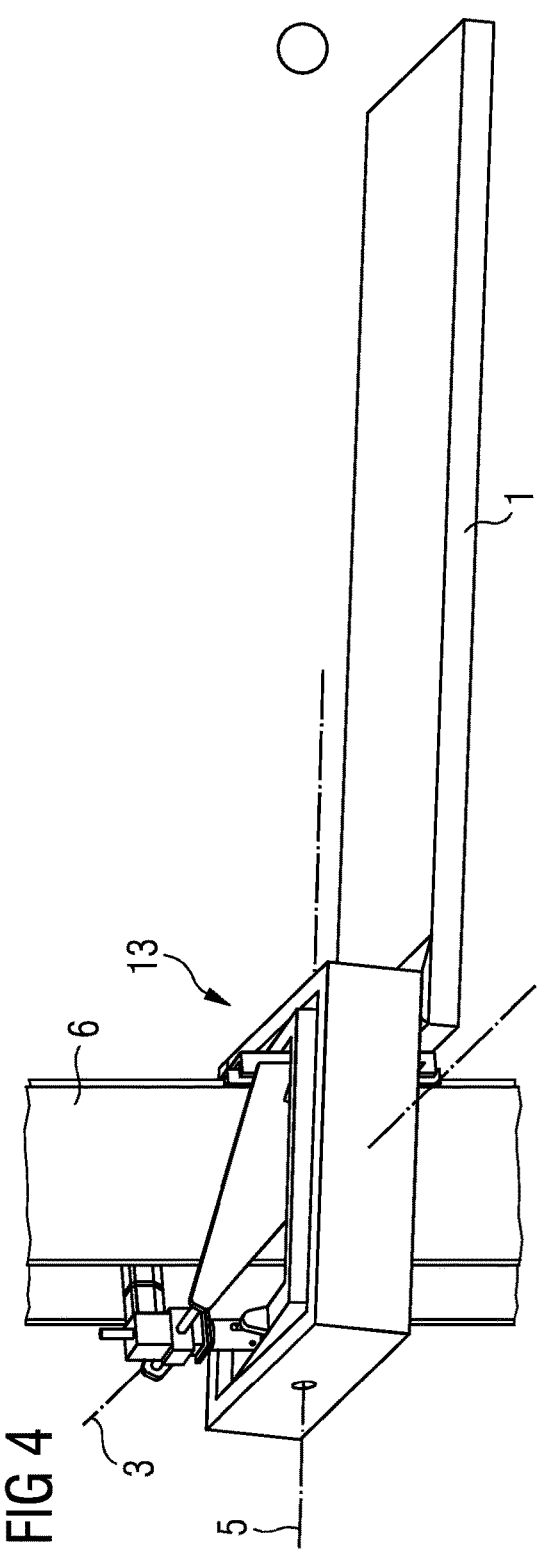

PATIENT SUPPORT APPARATUS WITH SIX DEGREES OF FREEDOM

CROSS REFERENCE TO RELATED APPLICATIONS

This application claims the benefit of DE 102016219162.4, filed on Oct. 4, 2016, which is hereby incorporated by reference in its entirety.

FIELD

Embodiments relate to a patient support apparatus including six degrees of freedom for inclining a patient couch and a method for inclining a patient couch using the patient support apparatus.

BACKGROUND

When treating tumors by radiotherapy using photon or particle beams, a patient is positioned precisely relative to a fixed or movable beam source in up to six degrees of freedom and, if applicable, to move the patient along defined trajectories during the radiotherapy. Planning algorithms are used to determine the positions and trajectories that, in combination with the radiation that is modulated in terms of intensity and energy of the photons or particles, will achieve a desired dose distribution in the patient tissue to be treated.

Patient support apparatuses including six degrees of freedom are provided for supporting the patient. Traditional patient support apparatuses, also known as patient positioning tables, only include four degrees of freedom. The fifth degree of freedom (e.g., "tilt axis") is an inclined position of the patient in the longitudinal direction and is also denoted by the surgical term "Trendelenburg tilt". The sixth degree of freedom (e.g., "roll axis") is an inclined position of the patient in the transverse direction.

Patient support apparatuses in radiotherapy may be equipped with an additional attachment module in order to obtain the fifth and sixth degrees of freedom. The modules are an attachment and, therefore, may restrict other treatment positions and are not part of the patient support apparatus.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a space-saving and robust patient support apparatus including six degrees of freedom and a method for inclining such a patient support apparatus.

In an embodiment, the patient support apparatus includes a single gimbal mount including two rotary frames arranged one inside the other for the fifth and sixth degrees of freedom for inclining a patient couch. The patient couch is arranged such that the patient couch is cantilevered on the gimbal mount, for example, at one of the two transverse sides.

Embodiments provide a patient support apparatus including a patient couch and a single supporting pillar, on which the patient couch is arranged in an adjustable and cantilevered manner. The patient support apparatus includes a first rotary frame that rotates about a first axis and encloses the supporting pillar. The patient support apparatus includes a second rotary frame that rotates about a second axis and rotatably encloses the first rotary frame and is fastened to the patient couch. The first rotary frame and the second rotary frame form a gimbal mount for the patient couch.

Embodiments provide for rolling and tilting a patient couch in a robust and safe manner. Different combinations of roll and tilt are possible. A dynamic movement about the two axes is also possible.

In an embodiment, the patient support apparatus includes a first mounting mechanism by which the first rotary frame is rotatably connected to the supporting pillar for rotation about the first axis.

In an embodiment, the patient support apparatus includes a second mounting mechanism, by which the second rotary frame is rotatably connected to the first rotary frame for rotation about the second axis.

In an embodiment, the patient support apparatus includes a first drive unit that is operatively connected to the first rotary frame so as to rotate the first rotary frame about the first axis.

In an embodiment, the patient support apparatus includes a second drive unit that is operatively connected to the second rotary frame so as to rotate the second rotary frame about the second axis.

In an embodiment, the first rotary frame and the second rotary frame may be rectangular.

Embodiments provide a method for inclining a patient support apparatus where the patient couch is tilted through a definable tilt angle about the first axis or the second axis.

Embodiments further provide a method for inclining a patient support apparatus where the patient couch is rolled through a definable roll angle about the first or second axis.

In an embodiment, the patient couch is tilted and rolled.

BRIEF DESCRIPTION OF THE FIGURES

FIG. 1 depicts an example of a patient support apparatus where the patient couch is not inclined.

FIG. 2 depicts an example of a patient support apparatus including a patient couch that is tilted.

FIG. 3 depicts an example of a patient support apparatus including a patient couch that is rolled.

FIG. 4 depicts an example of a patient support apparatus including a patient couch that is tilted and rolled.

DETAILED DESCRIPTION

FIGS. 1 to 4 depict a patient support apparatus including a patient couch 1 in different inclined positions of the patient couch 1. The patient couch 1 is cantilevered and gimbal-mounted on a single supporting pillar 6. The patient couch 1 extends like a cantilever out of a gimbal mount 13. The patient couch 1 is connected to the gimbal mount 13 only at one side (e.g., a transverse side). The single supporting pillar 6 performs the movements of the first to fourth degrees of freedom. The gimbal mount 13 provides the fifth and sixth degrees of freedom (e.g., inclined positions of the patient couch 1).

The gimbal mount 13 includes an inner first rotary frame 2 that is pivotally fastened to the supporting pillar 6 by a first mounting mechanism 7 for rotation about the first axis 3. The first rotary frame 2 provides a tilting movement of the patient couch 1. The first rotary frame 2 is enclosed by the second rotary frame 4, which is rotatably fastened to the first rotary frame 2 by the second mounting mechanism 8 for rotation about the second axis 5. The second rotary frame 4 provides the rolling movement of the patient couch 1. The first mounting mechanism 7 includes a seat 11 that is connected to the first rotary frame 2, and a shaft 12 that transfers the tilting movement to the first rotary frame 2. The second mounting mechanism 8 is not visible.

A first drive unit 9 (e.g., an electric linear motor) that is fastened to the supporting pillar 6 tilts the first rotary frame 2 about the first axis 3 by the seat 11 and the shaft 12. A second drive unit 10 that is arranged in the second axis 5 between the first rotary frame 2 and the second rotary frames 4 rolls the second rotary frame 4 about the second axis 5.

The second drive unit 10 is, for example, an axial drive (e.g., a cycloidal transmission) that is flange-mounted to an electric motor. The axial drive also provides the axis of rotation. Alternatively, the second drive unit 10 may be a linear drive that lies between the two rotary frames 2, 4.

The supporting pillar 6 may be configured to have a rectangular cross-section. The first rotary frame 2 and the second rotary frame 4 may be rectangular. Alternatively, a circular construction is also possible.

FIG. 1 depicts the patient couch 1 in a position parallel to a floor surface. FIG. 2 depicts tilting of the patient couch 1 through a tilt angle. FIG. 3 depicts rolling of the patient couch 1 through a roll angle. FIG. 4 depicts a combination of tilt and roll. The patient couch 1 is rolled through a roll angle and tilted through a tilt angle.

Optionally, the movements of the first rotary frame 2 and the movements of the second rotary frame 4 may be interchanged (e.g. the first rotary frame rolls the patient couch 1, and the second rotary frame 4 provides the tilting).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A patient support apparatus comprising:
   a patient couch;
   a supporting pillar, on which the patient couch is arranged in an adjustable and cantilevered manner;
   a first rotary frame that is rotatable about a first axis and encloses the supporting pillar; and
   a second rotary frame affixed to the patient couch, the second rotary frame being rotatable about a second axis and rotatably enclosing the first rotary frame,
   wherein the first rotary frame and the second rotary frame form a gimbal mount for the patient couch.

2. The patient support apparatus of claim 1, further comprising:
   a mounting mechanism, by which the first rotary frame is rotatably connected to the supporting pillar for rotation about the first axis.

3. The patient support apparatus of claim 1, further comprising:
   a mounting mechanism, by which the second rotary frame is rotatably connected to the first rotary frame for rotation about the second axis.

4. The patient support apparatus of claim 2, further comprising:
   a mounting mechanism, by which the second rotary frame is rotatably connected to the first rotary frame for rotation about the second axis.

5. The patient support apparatus of claim 1, further comprising:
   a drive unit operatively connected to the first rotary frame so as to rotate the first rotary frame about the first axis.

6. The patient support apparatus of claim 2, further comprising:
   a drive unit operatively connected to the first rotary frame so as to rotate the first rotary frame about the first axis.

7. The patient support apparatus of claim 3, further comprising:
   a drive unit operatively connected to the first rotary frame so as to rotate the first rotary frame about the first axis.

8. The patient support apparatus of claim 1, further comprising:
   a drive unit operatively connected to the second rotary frame so as to rotate the second rotary frame about the second axis.

9. The patient support apparatus of claim 2, further comprising:
   a drive unit operatively connected to the second rotary frame so as to rotate the second rotary frame about the second axis.

10. The patient support apparatus of claim 3, further comprising:
    a drive unit operatively connected to the second rotary frame so as to rotate the second rotary frame about the second axis.

11. The patient support apparatus of claim 5, further comprising:
    a drive unit operatively connected to the second rotary frame so as to rotate the second rotary frame about the second axis.

12. The patient support apparatus of claim 1, wherein the first rotary frame and the second rotary frame are rectangular.

13. The patient support apparatus of claim 2, wherein the first rotary frame and the second rotary frame are rectangular.

14. The patient support apparatus of claim 3, wherein the first rotary frame and the second rotary frame are rectangular.

15. The patient support apparatus of claim 5, wherein the first rotary frame and the second rotary frame are rectangular.

16. The patient support apparatus of claim 8, wherein the first rotary frame and the second rotary frame are rectangular.

17. A method for inclining a patient support apparatus, the patient support apparatus comprising a patient couch, a supporting pillar, on which the patient couch is arranged in an adjustable and cantilevered manner, a first rotary frame that is rotatable about a first axis and encloses the supporting pillar, and a second rotary frame affixed to the patient couch, the second rotary frame being rotatable about a second axis and rotatably enclosing the first rotary frame, wherein the first rotary frame and the second rotary frame form a gimbal mount for the patient couch, the method comprising:
    tilting the patient couch through a definable tilt angle about the first axis or the second axis.

18. The method of claim 17, further comprising:
rolling the patient couch through a definable roll angle about the first axis or the second axis.

* * * * *